(12) United States Patent
Wershofen et al.

(10) Patent No.: US 8,445,713 B2
(45) Date of Patent: May 21, 2013

(54) CATALYST FOR THE SYNTHESIS OF ORGANIC CARBONATES, PROCESS FOR PREPARING THE SAME AND APPLICATION THEREOF

(75) Inventors: Stefan Wershofen, Mönchengladbach (DE); Stephan Klein, Shanghai (CN); Zhiping Zhou, Shanghai (CN); Xinkui Wang, Shanxi (CN); Junwei Wang, Shanxi (CN); Maoqing Kang, Shanxi (CN)

(73) Assignee: Bayer MaterialScience AG, Leverkusen (DE)

( * ) Notice: Subject to any disclaimer, the term of this patent is extended or adjusted under 35 U.S.C. 154(b) by 232 days.

(21) Appl. No.: 12/738,687

(22) PCT Filed: Oct. 17, 2008

(86) PCT No.: PCT/EP2008/008793
§ 371 (c)(1),
(2), (4) Date: Aug. 4, 2010

(87) PCT Pub. No.: WO2009/052996
PCT Pub. Date: Apr. 30, 2009

(65) Prior Publication Data
US 2010/0312001 A1    Dec. 9, 2010

(30) Foreign Application Priority Data
Oct. 22, 2007  (CN) .......................... 2007 1 0047306

(51) Int. Cl.
| C07C 69/96 | (2006.01) |
| C07C 271/12 | (2006.01) |
| C01F 17/00 | (2006.01) |

(52) U.S. Cl.
USPC ............ 558/277; 558/260; 423/263; 560/115

(58) Field of Classification Search
USPC .................... 558/277, 260; 423/263; 560/115
See application file for complete search history.

(56) References Cited

U.S. PATENT DOCUMENTS

| 5,534,649 A | 7/1996 | Cho et al. |
| 5,565,603 A | 10/1996 | Saleh et al. |
| 6,010,976 A | 1/2000 | Ryu |
| 2006/0047136 A1* | 3/2006 | Sun et al. ...................... 558/277 |

FOREIGN PATENT DOCUMENTS

| EP | 460735 A2 | 12/1991 |
| EP | 742198 A1 | 5/1995 |
| EP | 505374 B1 | 4/1997 |
| WO | 9517369 | 6/1995 |

OTHER PUBLICATIONS

Tomishige et al., Catalyst Letters 76, No. 1-2, 71-74 (2001).*
Wang, Mouhua et al, "Synthesis of Dimethyl Carbonate from Urea and Methanol Over ZnO", Ind. Eng. Chem. Res. 2005, 44, pp. 7596-7599.
Wang, Mouha et al, "Synthesis of dimethyl carbonate from urea and methanol over solid base catalysts", Catalysis Communications, vol. 7, 2005, pp. 6-10.

* cited by examiner

*Primary Examiner* — Chih-Min Kam
(74) *Attorney, Agent, or Firm* — Lyndanne M. Whalen

(57) ABSTRACT

The present invention relates to a catalyst for the synthesis of organic carbonates, the preparation of the catalyst and the application of this catalyst in the synthesis of organic carbonates from reacting urea and hydroxyl group containing compounds. The catalyst provided in this invention is a calcinate of hydrous salt containing rare earth element at a moderate calcining temperature.

5 Claims, No Drawings

CATALYST FOR THE SYNTHESIS OF ORGANIC CARBONATES, PROCESS FOR PREPARING THE SAME AND APPLICATION THEREOF

The present application is a 371 of PCT/EP08/08793, filed Oct. 17, 2008.

TECHNICAL FIELD

The present invention relates to a catalyst for the synthesis of organic carbonates, the preparation of the catalyst and the application of this catalyst in the synthesis of organic carbonates.

BACKGROUND OF THE INVENTION

Organic carbonates are important intermediates in the chemical field, and can be used as reagents in methylation and carbomethoxylation reactions for the preparation of phenol ethers, quaternary salts of ammonium, ureas, urethanes, isocyanates and polycarbonates. These wide applications constitute a great need for the commercial production of organic carbonates. Much effort has been dedicated to develop the technologies for producing organic carbonates.

Take the production of dimethyl carbonate (DMC) for example. DMC is the lowest homologue of the family of dialkyl carbonates and is used widely in various organic syntheses. Traditionally DMC is industrially produced by the phosgenation of methanol. This method is gradually phased out due to the toxicity of phosgene and the need for corrosion resistant reactors.

There are two other commercialized technologies for producing DMC. One is the oxidative carbonylation of methanol using cuprous chloride as catalyst in a slurry reaction system, which is disclosed in EP 0 460 735 A2. However, the low per-pass conversion and difficult separation of catalyst from the product have been major problems requiring solution. The other one is a vapor-phase process using palladium catalyst and methyl nitrite promoter, which is disclosed in EP 0 742 198 A2 and EP 0 505 374 B1. Although the method is more promising, it involves the use of two separate reactors with two separate reaction schemes.

Besides the above-mentioned technologies being industrially exploited, many other alternative processes have been proposed recently. One of them is the alcoholysis of urea to dimethyl carbonate. In this process, in the presence of catalyst, methanol first reacts with urea producing methyl carbonate (MC), then MC formed further reacts with methanol to form target product, DMC.

The appropriate catalyst is crucial in the conversion from MC to DMC. Organotin compounds or its combination with co-catalysts are proposed in WO9,517,369, U.S. Pat. Nos. 5,565,603 and 6,010,976. The major disadvantages of this kind of catalysts are their high price and the difficult separation of the catalysts from the products. In addition, the preparation of this kind of catalysts is more troublesome. Other catalysts such as $K_2CO_3$, $CH_3ONa$ etc. are disclosed in U.S. Pat. No. 5,534,649, and ZnO in "Synthesis of Dimethyl Carbonate from Urea and Methanol over ZnO" by Wang MH et al, MCR, vol 44 7596-7599, 2005, and CaO in "Synthesis of Dimethyl Carbonate from Urea and Methanol over Solid Base Catalysts" by the same author, Catal Commun, vol 7, pp 6-10, 2006. But the DMC yields with these catalysts are low.

Thus the object of this present invention is to provide a catalyst for synthesizing organic carbonates which is prepared easily, and brings high yield and gives no pollution to the environments, and further objects are to provide the process to prepare such catalyst and the application of the catalyst in the production of organic carbonates.

SUMMARY OF THE INVENTION

The present invention provides a catalyst for the synthesis of an organic carbonate from reacting urea and hydroxyl group containing compounds. According to the embodiments of this invention, the catalyst comprises a calcinate prepared by calcining a rare earth element containing hydrous salt at a calcining temperature within the range of 150° C. to 450° C.

The present invention further provides a process for preparing such a catalyst. According to the embodiments of this present invention, the process comprises the step of calcining a rare earth element containing hydrous salt at a calcining temperature within the range of 150° C. to 450° C.

The present invention further provides a process for the synthesis of an organic carbonate. According to the embodiments of this invention, the synthesis process comprises the step of reacting urea with a hydroxyl group containing compound in the presence of a catalyst, said catalyst comprising a calcinate prepared by calcining a rare earth element containing hydrous salt at a calcining temperature within the range of 150° C. to 450° C.

Preferably the rare earth element is yttrium, lanthanum, cerium, praseodymium, neodymium, samarium, europium, gadolinium, terbium, dysprosium, holmium, erbium, ytterbium, thorium or mixtures thereof. More preferably the rare earth element is yttrium, lanthanum, praseodymium or mixtures thereof, and most preferably, yttrium, lanthanum or mixtures thereof.

The calcining temperature is preferred within the range of 300° C. to 350° C. The calcining time is preferred a period of 1 to 10 hours and more preferred 2-6 hours. The preferred calcining atmosphere is air, nitrogen, a noble gas, any non-oxidizing, any non-reducing gas, an oxidizing atmosphere, oxygen or an oxygen containing gas, or their mixtures, preferably air and/or nitrogen.

The quantity of the catalyst used in the process of synthesizing organic carbonates in this present invention is preferably up to 20%, more preferably 5-15% and most preferably 7-12% based on the weight of urea applied. The reaction temperature of synthesizing the organic carbonate is preferably 100-250° C., more preferably 120-230° C., and most preferably 160-180° C. The reaction pressure is preferably 1-30 atm, and more preferably about 5 to 20 atm, and it also may be the pressure autogenously developing at the chosen reaction temperature. The reaction time is about up to 10 hours, preferably 1-6 hours, and most preferably 2-4 hours.

Comparing to the prior art, the catalyst precursor is easily available and the preparation of the catalyst is simple. Moreover, the synthesis process with the catalyst has a high yield of organic carbonates.

The above and other characteristics, features and advantages of the present invention will become apparent from the following detailed description with the examples, which illustrate, by way of example, the principles of the invention. This description is given for the sake of example only, without limiting the scope of the invention.

DETAILED DESCRIPTION OF THE INVENTION

Suitable catalyst precursors for preparing the catalyst provided in the present invention are rare earth elements containing hydrous salts, which are easily available commercially.

The rare earth elements incorporated in the hydrous salts includes yttrium, lanthanum, cerium, praseodymium, neodymium, samarium, europium, gadolinium, terbium, dysprosium, holmium, erbium, ytterbium, thorium, or mixtures of two or more of the aforementioned elements. Especially preferred rare earth elements are those with trivalence, such as lanthanum, praseodymium and yttrium. Mostly preferred are lanthanum and yttrium.

The anions of the hydrous salts comprise those known anions in the art. Preferably they are selected from the group comprising nitrate, sulfate, halide—that is fluoride, chloride, bromide, iodide—,phosphate, acetate and mixtures of two or more of the aforementioned anions. Among them, nitrate and chloride are more preferred and nitrate is the most preferred.

These suitable catalyst precursors are preferably employed without pretreatment prior to the catalyst preparation.

The preparation of the catalyst comprises calcining the suitable catalyst precursors. Suitable calcining temperature according to embodiments of the present invention is within the range of 150-450° C. and preferably 300-350° C. The calcination temperature is a critical parameter in the process of preparing the catalyst. Different calcination temperatures result in the distinct evolution of precursor structure and disparate catalytic performance. The calcining temperature has to be sufficient to result in the transformation of the catalyst precursor to the catalyst, but too high calcining temperature may deteriorate performance of the catalyst.

Suitable calcining time according to preferred embodiments of the invention is 1-10 hours, preferably 2-6 hours, and superfluous calcination time is not necessary.

Preferably, the calcination is carried out in an oxidizing atmosphere. The oxidizing atmosphere is provided by oxygen or an oxygen containing gas, e.g. preferably air. The calcination can also be carried out in an inert atmosphere, and the inert atmosphere can be nitrogen, a noble gas, any non-oxidizing, any non-reducing gas or a mixture of two or more of the aforementioned components, and among them, nitrogen is the preferred constituent of the inert atmosphere.

In the presence of the catalyst provided according to this invention, urea reacts with hydroxyl group containing compounds to synthesize organic carbonates.

Urea employed for the synthesis of organic carbonates can be commercially available grades, and preferably, the purity of the urea is more than 99.5% by weight.

Suitable hydroxyl group containing compounds for the synthesis of organic carbonates comprise aliphatic alcohols, cycloaliphatic alcohols, araliphatic alcohols. The hydroxyl group containing compounds can contain one, two or more hydroxyl groups, which can be primary, secondary or tertiary hydroxyl groups.

The aliphatic alcohols suitable for the synthesis of the organic carbonates comprise methanol, ethanol, 1-propanol, 2-propanol, 1-butanol, 2-butanol, tert-butanol, pentanol or its isomers, hexanol or its isomers, and their higher homologues as well as their isomers. Examples of diols comprise ethylene glycol and propylene glycol.

The cycloaliphatic alcohols suitable for synthesizing the organic carbonates comprise cyclopentanol, cyclohexanol or their additional organic substituents containing derivatives.

The araliphatic alcohols suitable for synthesizing the organic carbonates comprise benzyl alcohol, 1-phenyl ethanol, 2-phenyl ethanol and their additional organic substituents containing derivatives.

Another group of hydroxyl group containing compounds suitable for the reaction comprises derivatives of the aforementioned hydroxyl group containing compounds where one or more of the hydrogen atoms directly connected to a carbon atom of said hydroxyl group containing compounds is substituted by one or more atoms, such as fluorine, chlorine, bromine or iodine.

The amounts of the raw materials are employed in such a way that at least two moles of hydroxyl groups coming from the hydroxyl group containing compound(s) are present for each mole of urea. It is preferred to apply an excess, that is, more than 2 moles of hydroxyl groups coming from the hydroxyl group containing compound(s) per mole of urea. It is more preferred to apply at least 4 moles of hydroxyl groups and most preferred to apply at least 10 moles of hydroxyl groups coming from the hydroxyl group containing compound(s) per mole of urea.

The amount of the catalyst used in the process should be sufficient to react urea with the hydroxyl group containing compound to synthesize organic carbonates. The amount of catalyst used in the process is preferably up to 20% by weight of urea used, more preferably 5-15% and most preferably 7-12%. From the examples below, a skilled person can easily know that an amount above 20% reasonably can also work in the process of synthesizing organic carbonates.

The catalyst can be present in the reaction mixture either as homogeneous catalyst or as heterogeneous catalyst or as partially homogenized catalyst. Heterogeneous catalyst can be employed as fixed bed, fluidized bed or slurry.

It is possible to use any additional solvents which are inert under the reaction conditions. Non limiting examples of such solvents are aromatic or aliphatic hydrocarbons, halogenated aromatic or aliphatic hydrocarbons, and ionic liquids.

The synthesis of organic carbonates can be carried out continuously, semi-continuously or batch-wise. The order of the addition of the raw materials and the catalyst to the reactor is not critical, and the best way to add the raw materials and the catalyst can be determined in orienting experiments. Alternatively, the ammonia formed during the reaction of urea and hydroxyl group containing compounds can be removed from the reactor by appropriate means continuously or intermittently to shift the reaction equilibrium to the product side.

The temperature for the reaction of urea and hydroxyl group containing compounds is preferred above 100° C. but not exceed 250° C. If the reaction temperature is too low, the reaction rate might be reduced too much, while at a too high reaction temperature the risk of unwanted side reaction significantly reducing yield and/or selectivity increases. The preferred range of the reaction temperatures is 120-230° C.; the most preferred range is 160-180° C.

The reaction pressure is the autogenous pressure developing at the chosen reaction temperature. Alternatively, the pressure can also be modified by adding an inert gas, like nitrogen, a noble gas, carbon dioxide, any other gas inert under the reaction conditions or mixtures of two or more of the aforementioned compounds to the reaction mixture. The reaction pressure is generally about 1 to 50 atm, preferably about 1 to 30 atm and more preferably about 5 to 20 atm.

The reaction time needed depends on the reaction conditions and the raw materials used. In general, the higher the molecular weight of hydroxyl group containing compound, the longer is the reaction time needed. The reaction time is up to 10 hours, preferably 1-6 hours, and most preferably 2-4 hours.

After the reaction is completed, the reaction mixture is removed from the reactor, and work-up and/or product isolation can be achieved by distillation, crystallization, filtration or other means or by combination of two or more of the aforementioned techniques/means.

The unreacted excess of the hydroxyl group containing compound(s), the catalyst as well as carbamates formed as intermediates in the reaction can be recovered and reused in the process.

The following examples further illustrate detailed for the process of this invention. The invention, which is set forth in the forgoing disclosure, is not to be limited either in spirit or scope by these examples. Those skilled in the art will readily understand that known variations of the conditions of the following procedures can be used.

EXAMPLES

The working examples underneath were carried out in an autoclave reactor equipped with a thermometer, a magnetic stirrer and a reflux column. The inner volume of the reactor was 100 ml. The hydroxyl group containing compound, urea, and catalysts were charged into the reactor. By flushing the reactor with $N_2$, the air within the autoclave was replaced. The reactor was heated to the desired temperature for a defined period of time as indicated in the examples. The by-product ammonia was released during the reaction using a valve located on top of the reflux column. After the reaction is completed, products obtained were analyzed by chromatography. Yields of carbonates like DMC and carbamates like MC (methyl carbamate) were calculated based on the weight of urea used.

Example 1

The catalyst was prepared by calcining the catalyst precursor $La(NO_3)_3 \cdot 6H_2O$ at a calcining temperature of 350° C. for a calcining time of 4 hours in air.

54.0 g of methanol, 6.0 g of urea and 0.5 g (i.e. 8.3% of the weight of urea) of catalyst as prepared above were charged into the reactor. The reaction was performed at 170° C for 4 hours under autogenous pressure (ca. 19.5 atm). The by-product ammonia was released through the valve above the reflux column during the reaction.

Yields of DMC and MC were 53.4 wt% and 41.2 wt%, respectively.

Example 2

Similar to EXAMPLE 1 except that the calcining temperature is 150° C.

Yields of DMC and MC were 45.5 wt% and 50.3 wt%, respectively.

Example 3

Similar to EXAMPLE 1 except that the calcining temperature is 450° C.

Yields of DMC and MC were 25.5 wt% and 70.4 wt%, respectively.

Example 4

Similar to EXAMPLE 1 except that the calcining time is 2 hours.

Yields of DMC and MC were 43.5 wt% and 46.7 wt%, respectively.

Example 5

Similar to EXAMPLE 1 except the calcining time is 6 hours.

Yields of DMC and MC were 51.6 wt% and 40.2 wt%, respectively.

Example 6

Similar to EXAMPLE 1 except the amount of catalyst used for the DMC synthesis was 0.3 g (i.e. 5% of the weight of urea).

Yields of DMC and MC were 42.6 wt% and 51.7 wt%, respectively.

Example 7

Similar to EXAMPLE 1 except that the amount of catalysts used was 0.9 g (i.e. 15% of the weight of urea).

Yields of DMC and MC were 52.2 wt% and 40.4 wt%, respectively.

Example 8

Similar to EXAMPLE 1 except that the catalyst precursor used was $Y(NO_3)_3 \cdot 6H_2O$.

Yields of DMC and MC were 49.6 wt% and 45.1 wt%, respectively.

Example 9

Similar to EXAMPLE 1 except that the catalyst precursor used was $Nd(NO_3)_3 \cdot 6H_2O$.

Yields of DMC and MC were 48.5 wt% and 44.6 wt%, respectively.

Example 10

Similar to EXAMPLE 1 except that the catalyst precursor used was $LaCl_3 \cdot 7H_2O$.

Yields of DMC and MC were 49.5 wt% and 34.2 wt%, respectively.

Example 11

The catalyst was prepared by calcining $Y(NO_3)_3 \cdot 6H_2O$ at a calcining temperature of 350° C. for a calcining time of 4 hours in air, same as EXAMPLE 8.

54.0 g of ethanol, 6.0 g of urea and 0.75 g of catalyst as prepared were charged into the autoclave. The reaction was performed at 180° C. for 4 hours under autogeneous pressure (ca. 14.6 atm)

Yields of diethyl carbonate (DEC) and ethyl carbamate (EC) were 62.4 wt% and 11.2 wt%, respectively.

Example 12

The catalyst was prepared by calcining $La(NO_3)_3 \cdot 6H_2O$ at 350° C. for 4 hours in air, same as EXAMPLE 1.

48.0 g of propanol, 6.0 g of urea and 0.8 g (i.e. 13.3% of the weight of urea applied) of catalyst as prepared were charged into the autoclave. The reaction was performed at 180° C. for 6 hours under autogenous pressure (ca. 12.2 atm).

Yields of dipropyl carbonate (DPC) and propyl carbamate (PC) were 54.2 wt% and 18.3 wt%, respectively.

Example 13

The catalyst was prepared by calcining $Yb(NO3)3.6H2O$ at 350° C. for 4 hours in air.

48.0 g of butanol, 6.0 g of urea and 0.75 g of catalyst as prepared were charged into the autoclave. The reaction was performed at 180° C. for 6 hours under autogeneous pressure (ca. 8.5 atm).

Yields of dibutyl carbonate (DBC) and butyl carbamate (BC) were 43.1 wt% and 12.8 wt%, respectively.

Example 14

Similar to EXAMPLE 1 except the amount of catalyst used for the DMC synthesis was 0.1 g (i.e. 1.67% of the weight of urea).

Yields of DMC and MC were 40.8 wt% and 48.1 wt%, respectively.

Example 15

Similar to EXAMPLE 1 except the amount of catalyst used for the DMC synthesis was 1.2 g (i.e. 20% of the weight of urea).

Yields of DMC and MC were 54.7 wt% and 24.6 wt%, respectively.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A process for preparing a catalyst for the synthesis of an organic carbonate, comprising the step of calcining a rare earth element containing hydrous salt at a calcining temperature within the range of 150° C. to 450° C. wherein said rare earth element is selected from the group consisting of yttrium, praseodymium, neodymium and mixtures thereof, and wherein said hydrous salt is selected from the group consisting of nitrate, sulfate, halide, phosphate, acetate and mixtures thereof.

2. The process as claimed in claim 1, wherein said calcining temperature is within the range of 300° C. to 350° C.

3. The process as claimed in claim 1, wherein the calcination time is within the range of 1 to 10 hours.

4. The process as claimed in claim 3, wherein the calcination time is within the range of 2 to 6 hours.

5. The process as claimed in claim 1, wherein the calcination is performed in the atmosphere selected from the group consisting of oxygen, air, nitrogen, a noble gas, and mixture thereof.

* * * * *